(12) United States Patent
Strehler

(10) Patent No.: US 9,163,207 B2
(45) Date of Patent: Oct. 20, 2015

(54) ANAEROBIC TREATMENT SYSTEM AND DEVICE

(75) Inventor: Benjamin Strehler, Ottawa (CA)

(73) Assignee: CH-FOUR BIOGAS, LLC, Fairfield, VT (US)

( * ) Notice: Subject to any disclaimer, the term of this patent is extended or adjusted under 35 U.S.C. 154(b) by 0 days.

(21) Appl. No.: 13/515,750

(22) PCT Filed: Nov. 29, 2010

(86) PCT No.: PCT/CA2010/001893

§ 371 (c)(1),
(2), (4) Date: Sep. 28, 2012

(87) PCT Pub. No.: WO2011/072369

PCT Pub. Date: Jun. 23, 2011

(65) Prior Publication Data

US 2013/0011896 A1 Jan. 10, 2013

Related U.S. Application Data

(60) Provisional application No. 61/286,323, filed on Dec. 14, 2009.

(51) Int. Cl.
| C12M 1/00 | (2006.01) |
| C05F 17/00 | (2006.01) |
| C12M 1/107 | (2006.01) |
| C12M 1/12 | (2006.01) |
| C12M 1/04 | (2006.01) |
| C12P 5/02 | (2006.01) |

(52) U.S. Cl.
CPC ............ C12M 23/14 (2013.01); C05F 17/0027 (2013.01); C12M 21/04 (2013.01);
(Continued)

(58) Field of Classification Search
CPC .............................. C12M 23/14; C12M 23/24
USPC ................ 435/283.1, 297.1, 290.4, 290.1
See application file for complete search history.

(56) References Cited

U.S. PATENT DOCUMENTS

| 4,100,023 A | 7/1978 | McDonald |
| 4,437,987 A * | 3/1984 | Thornton et al. ............. 210/137 |

(Continued)

OTHER PUBLICATIONS

High Flow Woven Geotextiles. Data Sheet [online]. Bonar Technical Fabrics NV, 2012, [retrieved on Aug. 7, 2013 from the Internet: <URL: http://www.bonartf.com/en/x/61/hf—high-flow-woven-geotextiles>.*

(Continued)

*Primary Examiner* — Laura Schuberg
*Assistant Examiner* — Kara Johnson
(74) *Attorney, Agent, or Firm* — Gilberto M. Villacorta; Jessica A. Flores; FOLEY & LARDNER LLP

(57) ABSTRACT

An anaerobic organic substrate treatment system is provided which comprises digester tubes wherein an inner bag of the digester tube is used to collect the solids content of the waste and an outer bag of the digester tube is used to collect the liquid and gas leachate from waste slurry input into the digester tubes. The inner bag is permeable to both gas and liquid while the outer bag is impermeable to both gas and liquid and allows for collection of gas and liquid leachate in the outer bag. Collected gas and liquid leachate may then be drained and collected using a drainage and collection system. Following treatment, the outer bag may opened to retrieve the inner bag for retrieval of the treated solids substrate. The substrate may then be used as needed. In one variant, the outer bag is re-sealable and may be reused in further treatment operations. The anaerobic waste treatment system may be used to carry out such treatment operations as storage/hydrolysis, methanization, and/or digestate treatment.

6 Claims, 11 Drawing Sheets

(52) U.S. Cl.
CPC .............. *C12M 23/06* (2013.01); *C12M 23/24* (2013.01); *C12M 23/26* (2013.01); *C12M 23/58* (2013.01); *C12M 29/00* (2013.01); *Y02E 50/343* (2013.01); *Y02W 30/43* (2015.05); *Y02W 30/47* (2015.05)

(56) References Cited

U.S. PATENT DOCUMENTS 6,569,332 B2 * 5/2003 Ainsworth et al. ........... 210/603
6,730,225 B1 * 5/2004 Duke et al. ................... 210/610

OTHER PUBLICATIONS

Burke, Denis, Dairy Waste Anaerobic Digestion Handbook, Environmental Energy Company, pp. 1-54.
Siegrist et al., "Mathematical Model for Meso- and Thermophilic Anaerobic Sewage Sludge Digestion", Environ. Sci. Technol., vol. 36, 2002, 1113-1123.
International Preliminary Report on Patentability mailed Jun. 19, 2012 in International Application No. PCT/CA2010/001893.

* cited by examiner

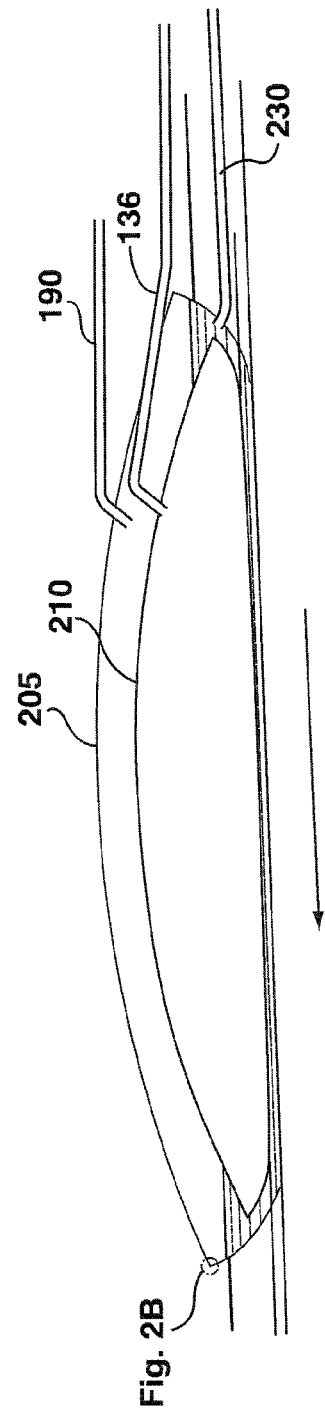
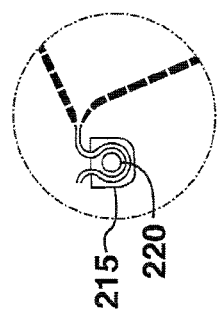
FIG. 2A
FIG. 2B

ANAEROBIC TREATMENT SYSTEM AND DEVICE

FIELD OF THE INVENTION

The invention relates to anaerobic treatment systems including digester systems and more specifically to anaerobic treatment systems which may be considered a hybrid batch and continuous digester system for storage/hydrolysis, mechanization and/or digestate treatment.

BACKGROUND

Anaerobic digestion is one system currently used as a sustainable way to deal with waste such as manure, crop residues, protein rich substrates, etc. Livestock manure has significant resource potential. It is a valuable source of crop nutrients and also represents a substantial bioenergy resource if processed by anaerobic digestion.

Using oxygen-free conditions, an anaerobic digester typically uses microorganisms to transform organic waste into biogas and soluble nutrients among others. Raw biogas typically consists of methane, carbon dioxide, water vapor, trace amounts of hydrogen sulfide and nitrogen. The biogas produced may be converted to electricity or collected and used as a direct energy source. Biogas may also be upgraded and fed into natural gas pipelines. Unlike fossil fuels, use of renewable resources represents a closed carbon cycle and therefore does not contribute to increases in atmospheric concentrations of carbon dioxide. In effect, anaerobic digestion is a carbon dioxide neutral solution.

The most common type of digester found on a farm is a complete mix digester. This digester is typically composed of a large round insulated concrete tank that sits above ground. A plastic membrane covers the tank in order to collect the produced biogas. The digester necessitates the use of liquid or slurry like substrates that contain 3% to 15% solids.

The complete mix digester functions with a continuous addition of substrate to the reactor. Once the substrate is in the digester, it is periodically agitated by a motorized mixer or a liquid recirculation pump. This helps to keep the solids in suspension, thus increasing the digester's efficiency. The complete mix digester supplies an eternal amount of biogas as long as new substrate is always added to the digester. This technology is suitable for slurries with a moisture content between 85% and 97%. However, substrates with large amounts of fiber or higher solid content are unsuitable because agitation becomes impossible or very energy intense.

Another type of digester is referred to as a batch digester and functions with batches of biomass. Typically, the batch digester has the same structural composition as the complete mix digester, however, there may or may not be agitation motion inside the digester. A large amount of waste such as manure is added to the digester at one time and it remains sealed until the end of the digestion process. After the digestion process it is removed and treated for other applications. The average retention time for a batch digester is typically 10 to 20 days. This enables the digestion to take place and sufficient biogas to be produced. However, the microbiology of the digester needs to constantly adapt to new environmental conditions, which makes the system less efficient.

Another type of digester is referred to as a plug flow digester and is typically composed mainly of a large rectangular tank that is dug into the ground. The tank is much longer than it is wide, typically approximately a 5 to 1 ratio, and is covered with an expandable plastic cover to retain the produced biogas.

Typically, the best substrate for the plug flow digester is manure with a sufficiently high solid content, usually from 11% to 14%. Most farmers therefore use scraped manure devoid of much of the bedding and containing substantially no sand. The plug flow digester typically does not have any internal agitation and instead, the manure flows through the digester. The constant addition and withdrawal of manure allows this displacement. However, there is always the possibility for some manure that floats on top or travels through the digester faster and some manure that settles to the bottom and remains in the digester. Usually the manure remains in the digester for 15 to 20 days before it is removed. Like other digesters, the plug flow digester collects the biogas produced by the manure. The biogas can then be extracted from the digester and used to generate electricity and heat. Again with a plug flow digester, the microbiology needs to constantly adapt to new environmental conditions, which makes the system less efficient.

One process that treats solid substrates is referred to as the garage type digester. These digesters consist of a large airtight compartment that typically resembles a garage. The substrate contained in the digester is composed of 30% or more solid content. The addition of small amounts of fresh crops and wood to the substrate is also possible.

The solid substrates are added to the compartment in batches. Once filled, the digester will not be opened until the digestion process is complete. The substrate is lightly and equally sprayed with water from above. The water percolates through the biomass, digesting it and producing biogas. The water is then collected at the bottom of the compartment and pumped into a temporary storage tank. This water is used to continuously spray the biomass.

The retention time for this digester is longer than others, averaging at about 28 to 30 days. The temperature inside the digester is usually maintained at around 40° C. The biogas is collected at the top of the compartment. One downside of this process is that moving the substrates into the garage and out of it again is very labour intense. Further, storage is required for the digested material.

Another type of digester is referred to as a dry digester. The dry digester takes many forms. However, the predominant design remains a type of plug flow digester oriented in a vertical or horizontal position.

The substrates used for dry digesters can contain up to 15% to 45% solids. Farmers therefore often use a mix of silaged crops and solid manure to fill the digester. In the case of a vertical dry digester, such as the one built by DRANCO-FARM technology in Nünstedt, Germany, the biomass is added at the top and travels towards the bottom due to gravity only. The produced biogas is collected at the top of the digester. In a horizontal dry digester design, the biomass moves from one end of the tank to the other propelled by motor driven agitators. There is also a conveyor belt at the bottom of the tank that picks up any sediment. Usually the retention time for a dry digester is only 2 to 3 days due to the faster rate of displacement. These systems tend to be expensive and require mechanically moving parts exposed to the biogas.

A need exists to provide an anaerobic substrate treatment device, system and/or method that overcomes or mitigates at least one of the problems outlined above and/or is observed in the field.

SUMMARY OF INVENTION

An anaerobic waste treatment system is provided which comprises digester tubes wherein an inner bag of the digester tube is used to collect the solids content of the waste and an outer bag of the digester tube is used to collect the liquid and gas leachate from waste slurry input into the digester tubes. The inner bag is permeable to both gas and liquid, but retains solids, while the outer bag is impermeable to both gas and liquid and allows for collection of gas and liquid leachate in the outer bag. Collected gas and liquid leachate may then be drained and collected using a drainage and collection system. Following treatment, the outer bag may opened to retrieve the inner bag for retrieval of the treated solids substrate. The substrate may then be used as needed. In one variant, the outer bag is re-sealable and may be reused in further treatment operations. The anaerobic waste treatment system may be used to carry out such treatment operations as storage/hydrolysis, methanization, and/or digestate treatment.

In one illustrative embodiment there is provided an anaerobic treatment system for treating organic substrate, the system comprising:

i) a receiving tank for receiving the substrate to be treated and generating a slurry together with a liquid;

ii) a first digester tube in liquid communication with the receiving tank for receiving the slurry for storage/hydrolysis, the first digester tube comprising:

an inner bag permeable to gas and liquid and substantially impermeable to solids;

an outer bag housing the inner bag such that gas and liquid leaches from the inner bag to the outer bag, the outer bag impermeable to gas and liquid;

iii) a drainage system in communication with the outer bag, the draining system comprising a drain valve operable in a closed position for preventing draining of the outer bag and in an open position for draining the outer bag of leachate;

wherein, when the drainage system is closed, the slurry in the first digester tube is separated into leachate collected in the outer bag and substrate collected in the inner bag.

In another illustrative embodiment, the anaerobic treatment system outlined above, further comprises:

iv) a second digester tube in fluid communication with the receiving tank, the second digester tube comprising:

an inner bag permeable to gas and liquid and substantially impermeable to solids;

an outer bag housing the inner bag such that gas and liquid leaches from the inner bag to the outer bag, the outer bag impermeable to gas and liquid;

v) a drainage collection tank in fluid communication with the drainage system for receiving leachate drained from the digester tubes, the drainage collection tank in fluid communication with the receiving tank for recycling leachate to the receiving tank, and in fluid communication with the digester tubes for recycling leachate to the digester tubes;

wherein the second digester tube is suitable for methanization treatment of the slurry.

In another illustrative embodiment, the anaerobic treatment system outlined above further comprises:

vi) a third digester tube in fluid communication with the receiving tank, the second digester tube comprising:

an inner bag permeable to gas and liquid and substantially impermeable to solids;

an outer bag housing the inner bag such that gas and liquid leaches from the inner bag to the outer bag, the outer bag impermeable to gas and liquid;

wherein the drainage collection tank is in fluid communication with the inner bag of the third digester tube for recycling leachate from the second digester tube for digestate treatment with biologically activated sludge and a microorganism for digesting the leachate.

In another illustrative embodiment, the anaerobic treatment system outlined above the digester tubes are sloped towards one end for collecting the leachate and the draining system collects the leachate from the lower end.

In another illustrative embodiment, the anaerobic treatment system outlined above the inner bag is substantially impermeable to solids having a particle size greater than 0.425 mm.

In another illustrative embodiment, the anaerobic treatment system outlined above digester tube comprises:

i) an inner bag permeable to gas and liquid and impermeable to solids; and ii) an outer bag housing the inner bag such that gas and liquid leaches from the inner bag to the outer bag, the outer bag impermeable to gas and liquid.

In another illustrative embodiment, the anaerobic treatment system outlined above the outer bag is flexible and comprises a sealable opening for allowing removal of the inner bag, the sealable opening being liquid and gas impermeable when sealed.

In another illustrative embodiment, the anaerobic treatment system outlined above the sealable opening comprises a clip including a substantially circular opening for accommodating sides of the outer bag adjacent the opening and a hose insertable into the circular opening to cause a pressure fit between the hose, the clip and the sides of the outer bag adjacent the opening, the pressure fit suitable for imparting sufficient pressure to cause a seal impermeable to gas and liquid.

In another illustrative embodiment, the anaerobic treatment system outlined above the inner bag is substantially impermeable to solids having a particle size greater than 0.425 mm.

In another illustrative embodiment there is provided a method of anaerobically treating organic substrate comprising the steps of:

i) placing the substrate in an anaerobic environment;

ii) separating a fluid and gas component from the organic substrate thereby adjusting the pH of the substrate to a suitable level for treatment; and iii) hydrolysing, methanizing, or digesting the substrate.

In another illustrative embodiment, the method outlined above further comprises a step of adding microorganisms for carrying out step iii).

In another illustrative embodiment, in method outlined above at least of two of hydrolysing, methanizing or digesting is carried out, each treatment simultaneously in a separate anaerobic environment.

BRIEF DESCRIPTION OF THE DRAWINGS

FIG. 2A is a cross-sectional view illustrative of a digester tube suitable for carrying any one of storage/hydrolysis, methanization and digestate treatment; and FIG. 2B is a cross-sectional view illustrative of a clip system for a re-sealable outer bag of a digester tube.

DETAILED DESCRIPTION

Figure 1:
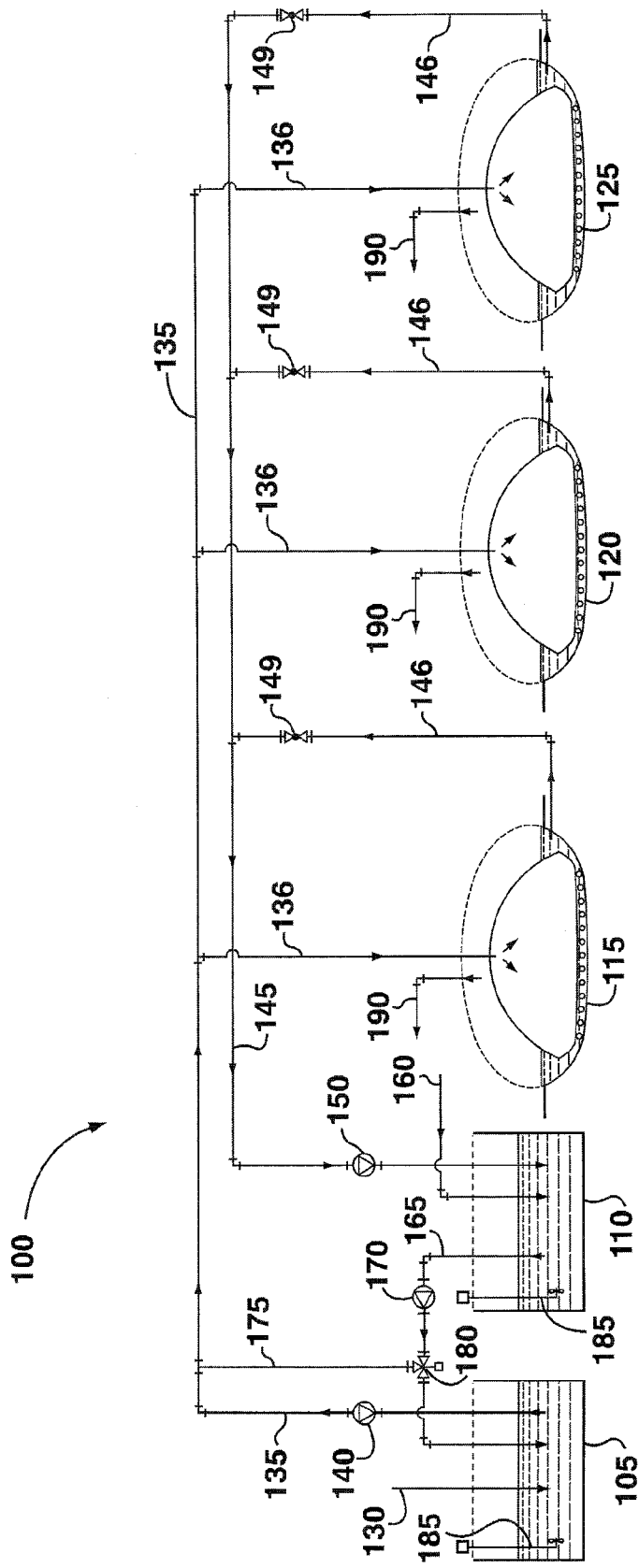
FIG. 1 is a schematic single line view illustrative of one embodiment of an anaerobic treatment system having a digester tube for each of treatment condition of storage/hydrolysis, methanization and digestate treatment.

An anaerobic treatment system for treating waste, such as a liquid or solid waste including organic substrate typically in the form of livestock waste or seasonal waste, is shown generally as 100 in FIG. 1. The system 100 shown in FIG. 1 is merely illustrative of an embodiment of a treatment system in accordance with the presence invention is not intended to be limiting.

The treatment system 100 includes a receiving tank 105 for receiving influent such as waste as outlined above, optionally together with a liquid and/or a suitable additive for breaking down the waste such as a microorganism as would be appreciated by one of skill in the art. A substantially homogenous slurry is generated in the receiving tank 105 using for example an agitator 185.

The treatment system 100 further includes at least one digester tube 115 for receiving the slurry from the receiving tank 105. Each digester tube 115 includes an inner bag 210 and an outer bag 205 as shown in FIG. 2. The inner bag 210 is permeable for liquid and gas and is substantially impermeable for solids. The inner bag 210 may have an apparent opening size of 0.425 mm. The outer bag 205 is impermeable to both gas and liquid in addition to solids. The digester tube 115 is in liquid communication with the receiving tank 105 via a supply line 135. The slurry is received into the inner bag 210 via the main supply line 135 in communication with the receiving tank 105 and branch supply line 136 branching off of the main supply line 135. Over time, the slurry is separated into a liquid and gas component which leaches through the permeable inner bag 210 and is collected in the outer bag 205. The collected liquid or leachate may be drained using a drainage system 146. The drainage system 146 includes a drain valve 149 and a return line 145, and is connected to the outer bag 205 in a position suitable for draining collected liquid from the outer bag 205 when the drain valve 149 is in an open position. The leachate from the digester tube 115 is directed via the draining system 146 into a draining collection tank 110 which is optionally connected to the receiving tank 105 and/or the main supply line 135 for recycling of leachate as will be described below. It will be appreciated by one of skill in the art that various supply line setups may be used for transferring waste slurry from the receiving tank 105 to digester tubes 115 and the setup shown in FIG. 1 may be altered without departing from the scope or spirit of the invention.

To allow for recycling of leachate from the drainage collection tank 110 to either the receiving tank 105 or the various digester tubes 115, 120, 125, etc., addition of microorganisms or other chemicals to the leachate and operation of the treatment system, other valves and/or piping may be required such as that shown in FIG. 1 such as valves 140, 150, 170 and 180, recycling pipes 165 and 175, chemical input pipe 160, etc. Further, biogas may be collected from the outer bag 205 of the digester tubes 115, 120 or 125 using a biogas outlet 190. The collected biogas may be used for example for applications known to those of skill in the art.

The system 100 is capable of performing different treatment operations and so the number of digester tubes 115 will vary depending for example on the treatment operation and volume of treatment required. There are three illustrative treatment operations which may be carried out and which require different numbers of digester tubes 115. For each treatment operation there may be multiple digester tubes required depending on the scale of the project. Not all of the treatments operations are essential to the system and the system may be modified based on the desired treatment operations to be carried out. The treatment operations include but are not limited to storage/hydrolysis, methanization, and digestate treatment. These treatment operations will be described in more detail below with reference to the system outlined in FIG. 1 with optional digester tubes 115, 120 and 125 indicated as necessary.

Storage/Hydrolysis

Some organic waste streams, such as organic yard waste, fruit processing waste or winery organics, require storage, since the biogas production should occur evenly over the course of the year, but the waste streams are only available over a few months. As a result, storage of the organic waste may be desired or necessitated.

In operation in a storage or hydrolysis mode, slurry is pumped from the receiving tank 105 to the digester tube 115 and into the inner bag 210. Once in the inner bag 210, the drain valve 149 is maintained in the closed position and the gas and liquid components of the slurry leach through the permeable inner bag 210 and are collected in the outer bag 205. Slurries with high amounts of organic substance will produce organic acids while stored, thus lowering the pH and enhancing hydrolysis.

While the drain valve 149 is closed, the substrate in the inner bag 210 may be stored in the absence of oxygen and in a closed controlled confinement until the activation of the anaerobic digestion process by introducing microorganisms or leaching out organic acids for raising the pH to induce a microorganism friendly environment. The microorganisms may form part of the organic waste being stored in the inner bag 210 or may be added to the slurry in the receiving tank 105. The anaerobic digestion process may also be activated by leaching out organic acids for raising the pH of the slurry to induce a microorganism friendly environment. The microorganisms directing hydrolysis typically do not function below a pH of 5, while the natural pH typically drops to about 4. As a result, the pH must be raised to facilitate hydrolysis, when then produces acids.

In order to produce a pH of approximately 5.5 in the hydrolyzer, the organic loading rate must be high enough such that acid-forming microorganisms can degrade the fibre, but low enough that the bacteria are not inhibited by the low pH. The pH will be controlled through the addition of digestate as a means of balancing the incoming substrate and maintaining a pH of 5.5.

The leachate may be drained by opening the drain valve 149 and the digester tube 115 may be loaded on an ongoing basis with different slurries, as the liquid drains out for further treatment or storage. As such, the inner bag 210 may be loaded on an ongoing basis with different slurries comprising different wastes until the inner bag 210 is full following draining of the liquid and gas from the inner bag 210 to the outer bag 205 and even following draining of the outer bag 205.

The drainage collection tank 110 receives leachate collected from the digester tube 115 which may then be pumped into the receiving tank 105 to create a slurry from incoming waste substrates in the case where the incoming waste substrates have a total solids content that is too high to form a pumpable slurry for being pumped into the digester tubes. Otherwise, the collected leachate in the draining collection tank 110 may be treated for the reduction of inhibitors, as outlined for example in *Anaerobic Digestion Model No. 1 (ADM1)*, IWA Task Group for Mathematical Modelling of Anaerobic Digestion Processes, Scientific and Technical Report No. 13, 2002, incorporated herein by reference, and pumped back into a digester tube 120 for methanization, diluting inhibitors inside the digester tube 115 or the treated collected leachate may be discharged for other application such as discharged into a lagoon storage for land application. A lagoon storage being a pond-like basin used to store digestate prior to land application.

Following storage/hydrolysis, the solids, typically being a mixture of substrate, inert materials and microorganisms are retained in the inner bag 210 until the inner bag 210 is full and the batch is finished and the solids may be land applied. At this time, the digester tube 115 may be opened to remove the accumulated solids inside the inner bag 210. The solids may be applied as is known by of skill in the art. The inner bag 210 is disposed of and replaced with a new inner bag 210 while the outer bag 205 is reusable. The digester tube 115 will be explained in more detail below with reference to FIG. 2.

By recycling the leachate collected in the outer bag 205, pH and substrate input may be adjusted as needed for achieving the desirable result, which may be maximum biogas yield, minimal chemical oxygen demand (COD) in the effluent, or acidification of the substrate for hydrolysis.

Methanization

Methanization is performed to produce methane gas which may then be used for in number of applications such as producing electricity or in any other combustion process.

In a digester tube 120, separate to the digester tube 115 used for storage/hydrolysis, methanization may be carried out. Alternatively, following storage/hydrolysis, methanization may be carried out using the solids remaining in the inner bag 210 of the digester tube 115. The solids, comprised of microorganisms, inert solids and organics with low degradability are retained in the inner bag 210 of a digester tube, for example 120. The liquid fraction of the slurry leaches out of the inner bag 210 and is collected in the outer bag 205 and is discharged through the drain system 146. The digester tube 120 may be sloped towards one end such that leachate pools in the lower end of the outer bag 205 of the digester tube 120 and is drained into the drainage collection tank 110 via the drainage system 146. The drain valve 149 is maintained in the opened position during methanization and digestate treatment. This is different from the storage phase wherein the drain valve 149 is maintained in the closed position and the hydrolysis phase wherein the drain valve 149 is operated at various times in either the opened or closed position.

In the methanization phase, the typical resulting pH is approximately 7.5. If the substrate is stored in a bunker silo, for example, with standard ensiling processes applied (i.e. fermentation), the resulting silage's pH is typically around 4.0. Substrate obtained from the hydrolysation phase typically has an incoming pH of about 5.5. Substrate from storage would be expected to be around 4 pH as when the valve is closed all the acids remain in the storage bag thus lowering the ph to about 4. By opening the valve and draining the leachate, containing fatty acids, and adding liquid with a higher pH, acids are washed out and the pH is consequently raising up to 5.5, where it is maintained by controlling the amount of liquid added. Note that pH 5.5 is not a stable state and must be managed by adding the appropriate amount of liquid. The fatty acids, responsible for the low pH, are converted into methane during the methanization, thus resulting higher in a higher pH during and after methanization.

Inside the digester tube 120, microorganisms present in the substrate or introduced specifically with the substrate, anaerobically decompose the substrate and attach to the solids with are retained with the inner bag 210 resulting in methanization. The microorganisms are known in the art and include those disclosed in *Anaerobic Digestion Model No. 1 (ADM1)*, IWA Task Group for Mathematical Modelling of Anaerobic Digestion Processes, Scientific and Technical Report No. 13, 2002 and *Mathematical Model for Meso- and Thermophilic Anaerobic Sewage Sludge Digestion*, Hansruedi Siegrist, et al, Environ. Sci. Technol. 2002, 36, 1113-1123 herein incorporated by reference.

Biogas such as methane may be vented from the digester tube 120 via a biogas outlet 190 and directed as desired for example to a collector.

After collection and drainage, leachate may be cycled through the digester tube 120 until a discharge criteria is achieved, with the microorganism inside the digester tube 120 acting as an active biofilter. The solid may be collected from the inner bag 210 and the inner bag discarded and replaced while the outer bag 205 may be reused.

Digestate Treatment

In situations when the liquid phase is to be discharged into surface water, strict regulations apply to maximal allowable COD (chemical oxygen demand). By using the digestate treatment function of the tube, the COD from the anaerobic digestion process can be lowered from about 25000 ppm to about 2000 ppm, which is close to typical discharge criteria (differs from jurisdiction to jurisdiction).

A third digester tube 125 may be used in conjunction with a methanization digester tube and optionally a storage/hydrolysis digester tube for carrying out digestate treatment. The third digester tube 125 is as described for example as above with reference to the storage/hydrolysis digester tube or the methanization digester tube or as described with reference to FIG. 2 below.

Leachate from the methanization process is pumped into the digester tube 125 for digestate treatment. The digester tube 125 for carrying out digestate treatment contains biologically activated sludge. The biologically activated sludge is sludge containing microorganisms suitable to perform methanization or hydrolysis. Microorganisms which digest the leachate are pumped into and dewatered by the inner bag 210. The COD thus can further lowered, while working with a liquid containing low amounts of solids. The biogas yield is typically lower compared to the methanization phase, but the effluent quality can be enhanced including a lower COD and lower ammonia concentrations. To capture nutrient value remaining in the substrate, potash can be removed by reverse osmosis.

To keep the microorganism activity optimal, a temperature of 40° C. should be maintained for hydrolysis, methanization and digestate treatment, but is not required for storage only. Hydronic heating at the bottom of the system between the outer bag 205 and the inner bag 210 provides for a stable temperature within the tube. Additionally, heating can be introduced in the receiving tank and the drainage collection tank.

Application of System

Various applications of an anaerobic treatment system of the present invention may be used and the following examples are meant to be illustrative and are not intended to be limiting.

Various types of waste substrate may be treated using an anaerobic treatment system of the present invention including for example but not limited to, seasonal organic waste, livestock manure such as poultry manure, protein rich substrates producing elevated levels of ammonium inhibiting the anaerobic digestion process, substrates containing heavy metals, which can be accumulated within the solid phase, compost, and waste water treatment sludge.

Seasonal substrates such as crop residues, garden and park wastes can be received, slurried up and stored inside a digester tube 115, where the pH is lowered by separation of the leachate and the substrate material undergoes a hydrolysis phase. The leachate can then be directed into a wet fermentation or introduced into a methanizing digester tube 120. The solids inside the digester tube 115 may used as anaerobic compost.

Poultry manure is usually much dryer compared to dairy or swine manure, typically containing over 50% dry matter compared to dry matter contents of typically less than 15% for dairy and swine. Poultry manure must be diluted prior to introduction it into a wet digestion reactor in order for it to be pumped. Using the anaerobic treatment system comprising digester tubes as described herein for poultry manure allows the liquid input to be kept minimal, as the liquid is reused. The typically high ammonia levels are washed out as described above as the solids are dewatered on an organic basis. Magnesium ammonium phosphate (MAP) may be precipitated allow for removal of ammonia and the liquid fraction can by recycled.

When proteins are anaerobically digested, the nitrogen is converted into ammonia through hydrolysis. Ammonia inhibits methanization already at low concentrations and its presence reduces the performance of anaerobic digestion.

Washing out the ammonia as described above through the recycling of the liquid and removing it in a separate reactor through struvite MAP precipitation will greatly enhance digestibility and thus allow anaerobic digestion of protein rich substrates. Using the digester tubes disclosed herein, the ammonia can be washed out of the substrate inside the tube in a controlled manner, allowing the concentration to remain low and below inhibition concentrations.

The presence of heavy metals can impose severe restrictions to land application of bio-solids. By lowering the pH through adding chemicals, the heavy metals can be mobilized into the liquid fraction and removed from the substrate in the inner bag of the digester tube through the drainage, and then precipitated in a second reactor.

The process of composting involves an aerobic treatment, whereby carbon compounds are converted into $CO_2$. No methane is produced in an aerobic reaction. Pumping the organic material into a digester tube instead allows the anaerobic degradation of the substrate and generates biogas (see *Dairy Waste Anaerobic Digestion Handbook*, Burke, Denis, Environmental Energy Company) which can be used energetically. The final product is similar to traditional compost.

Treatment and disposal, including land application of sewage sludge is of concern in many jurisdictions. The digester tubes and anaerobic treatment system allows anaerobic digestion, dewatering and storage of the sewage sludge in a single step.

Digester Tube

The digester tube shown with reference to FIG. 2 is illustrative of one embodiment of a digester tube and is not meant to be limiting.

FIG. 2 shows a cross-sectional view illustrative of one embodiment of a digester tube 200 for use in the anaerobic treatment of waste, such as for example that described above, in an anaerobic treatment system, such as for example that described above. The digester tube 200 includes an inner bag 210 for receiving waste substrate. The waste substrate may be received in a slurry form or any form suitable for delivery into the inner bag 210 of the digester tube 200. The inner bag 210 is captured within an outer bag 205. The inner bag 210 is comprised of a material permeable to both gas and liquid and impermeable to solids. The inner bag 210 contains permeations which typically prevent solids bigger than 0.425 mm from passing from the inner bag 210 to the outer bag 205. As such, liquid and gas from the waste substrate leach through the inner bag 210 and into the outer bag 205 where they collect as the outer bag 205 is impermeable to both liquid and gas as well as solids. Once collected in the outer bag 205, the leachate may be drained via a draining tube 230 inserted separately or incorporated into the outer surface of the outer bag 205. Further, a biogas outlet (shown in FIG. 1 as 190) may be inserted into the outer bag 205 to allow for collection of the biogas from the outer bag 205. The biogas outlet may be inserted separately into the outer bag 205 or may be incorporated into the outer bag 205. Alternatively, ports for receiving the biogas outlet 190 and/or the draining tube 230 may be incorporated into the outer surface of the outer bag 205 such that the outer bag 205 is maintained as impermeable to both gas and liquid upon insertion of the various components into the corresponding port.

The inner bag 210 may be comprised of a flexible geotextile such as a Geotube which allow for gas and liquid to permeate therethrough but is impermeable to solids. Upon completion of the waste slurry treatment, the inner bag 210 is removed from the outer bag, opened and the substrate removed and used accordingly. The inner bag 210 is the discarded as necessary.

The outer bag 205 may be comprised of a flexible material such as an EDPM membrane, which prevent both gas and liquid to be permeate therethrough. Upon completion of the waste slurry treatment, the outer bag 205 is opened and the inner bag 210 removed. In one variant, the outer bag 205 is openable to retrieve the inner bag 210 and in a further variant the outer bag 205 is sealingly openable to retrieve the inner bag 210 such that after removal of the inner bag 210 and input of a new inner bag 210, the outer bag 205 is re-sealed such that it is again impermeable to both gas and liquid. One re-sealable variant of an outer bag 205 comprises an opening sealable using a clip 215 which includes an substantially circular opening of accommodating sides of the outer bag 205 adjacent the opening and a hose 220 which slides through the circular opening creating a pressure seal between the hose 220, each side of the outer bag 205 adjacent the opening in the outer bag 205 and the clip 215. The clip 215 and the hose 220 are shown in cross section in FIG. 2B. The pressure fit once the hose 220 is in place in the clip 215 with the sides of the outer bag 205 is sufficient to create a seal against egress of both gas and liquid from the outer bag 205. By using a re-sealable outer bag 205, the outer bag 205 may be reused following replacement of the inner bag 210.

The outer bag may be 10% larger than the inner bag. Upon disposal, the inner bag geotextile may be reused in various applications such as for road construction are geotextile.

Test Data—Modeling of Anaerobic Digestion

Aquasim

Aquasim is a computer program designed to identify and simulate aquatic systems as they occur in laboratories, industrial facilities and natural environments. These models serve as tools to improve the research, design, operation and optimization of anaerobic processes under specific conditions. The computer program Aquasim was developed to perform such analyses for technical and natural aquatic systems. By defining compartment size and configuration along with the links of these various compartments in Aquasim, real-life situations can be simulated. Simulations produce data that suggests whether or not a real life situation is feasible, allowing for recommendations with regard to operational scenarios.

Models were configured for the digestion of chicken manure. Published data was used for definition of the substrate to calibrate the model. The calibrated model then simulated the digestion process in order to model future operations.

Substrate

The chicken manure substrate that was used for this model is composed of approximately 77% organic matter which can be broken down into proteins, lipids and carbohydrates. The breakdown is defined in Table 1:

TABLE 1

| Substrate Composition of Volatile Solids | |
| --- | --- |
| Proteins | 28.0% |
| Lipids | 10.0% |
| Carbohydrates | 39.0% |

The rate at which chicken manure is introduced into the anaerobic digester system (flow rate) is based on optimization of biogas production in the simulated system. If the input flow rate is set too high, system stability is negatively affected. If the input flow rate is too low, the biogas production will likely not justify the cost of the operation. The input of 10 $m^3$ of chicken manure/day was considered the optimal value of the system and was used as the input flow variable. This value, along with total solids content and chemical oxygen demand and any other relevant variables are required for Aquasim modeling.

System

Figure 3:
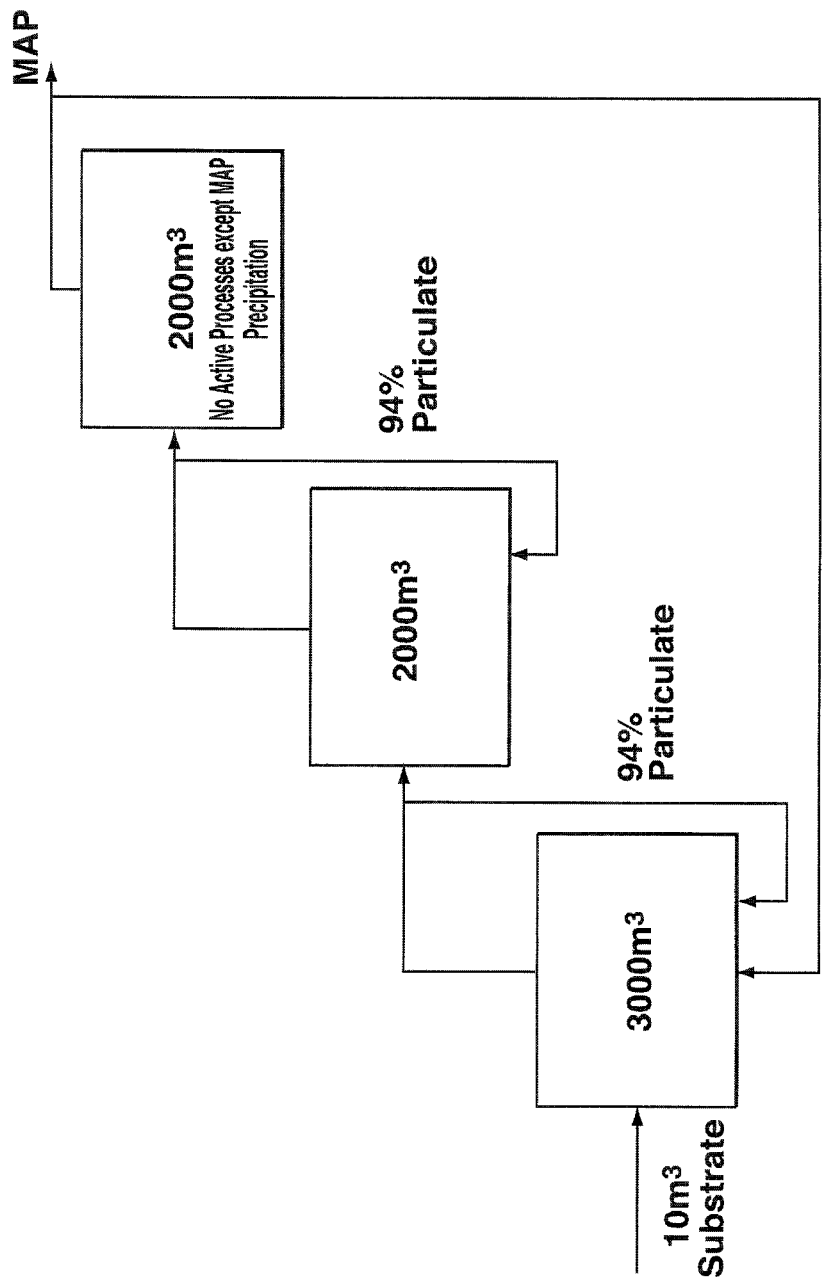
FIG. 3 is a diagram illustrating one example of a system layout used for data modelling.

The system configuration that was used to model the anaerobic digestion of chicken manure with active MAP precipitation involves three reactors connected in series with internal recycling of 94% of particulates (FIG. 3). Biogas is produced in both the first and second reactors, but not in the third reactor. In order to allow MAP precipitation to occur the following system configuration was used.

Results

Figure 4:
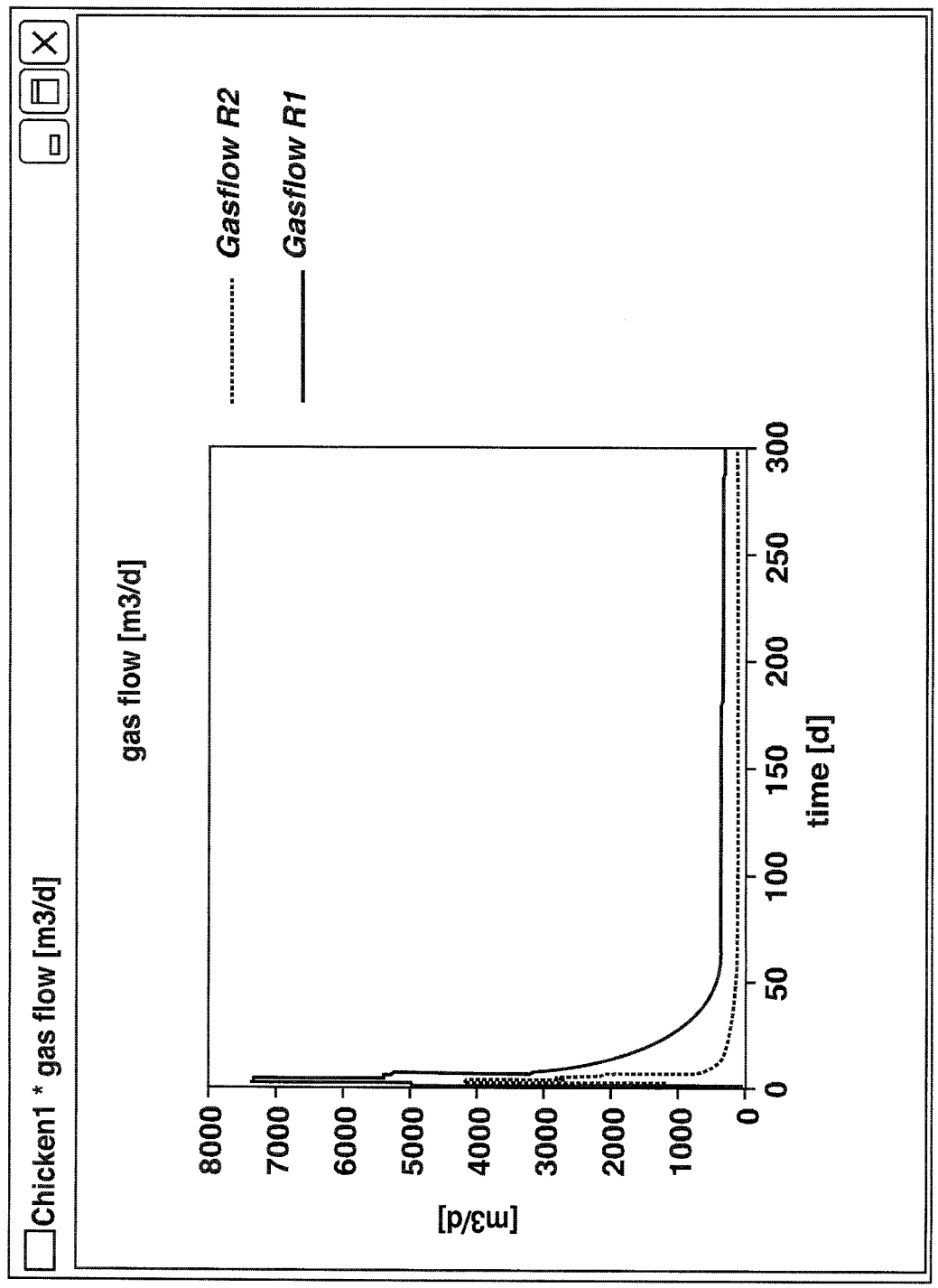
FIG. 4 is a graph illustrating modelling data of gas flow in Reactor 1 and Reactor 2.

Using the system configuration and substrate analysis described above the following graphs were created:

Daily Biogas production
Chemical Oxygen Demand
Organic Acids
Inhibition
Acidity (pH)
Precipitation
Ammonia Concentration Daily Biogas Production As seen in FIG. 4, gas flow of 470 $m^3$/day was achieved after approximately 50 days of operation. The data obtained from the first 40-50 days can be considered negligible as the system was in the process of stabilizing and does not necessarily reflect actual digester performance. The unbroken line represents the gas flow out of reactor 1 while the broken line is for the gas flow out of reactor 2.

FIG. 4 further indicates the total biogas production from Reactor 1 and Reactor 2 in $m^3$/day over 300 days. At 100 days, Reactor 1 has a gas flow of 358 $m^3$/day and Reactor 2 has a gas flow of 114 $m^3$/day.

Figure 5:
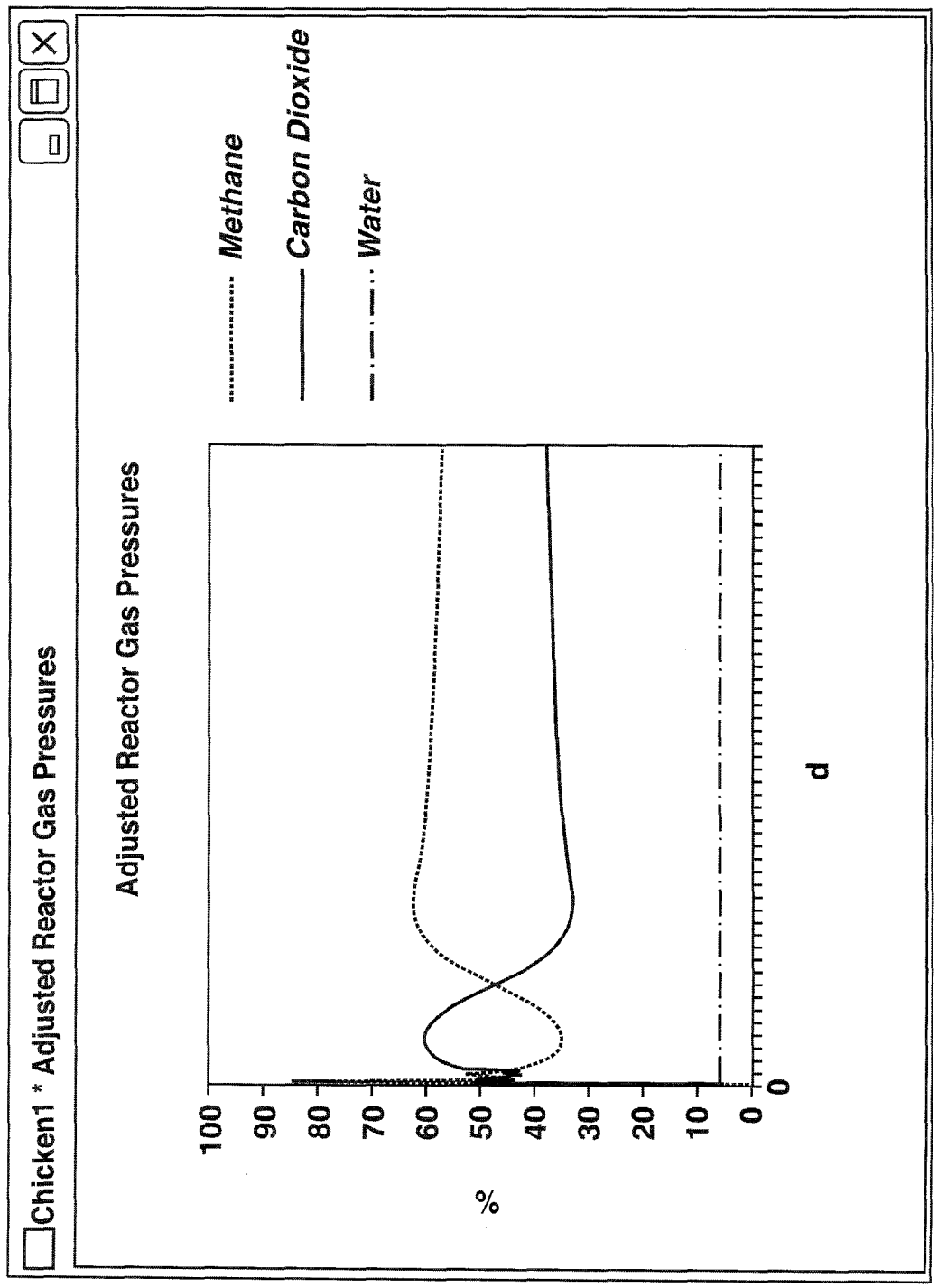
FIG. 5 is a graph illustrating modelling data of biogas composition of Reactor 1.

FIG. 5 shows the composition of the biogas that is produced in Reactor 1. A flow rate of 47 $m^3$ biogas per tonne of chicken manure was calculated with approximately 60% methane concentration, which matches the theoretical yield for chicken manure. Total gas flow of 470 $m^3$/day produces approximately 14,790 MBTU/day of energy.

Chemical Oxygen Demand (COD)

Figure 6:
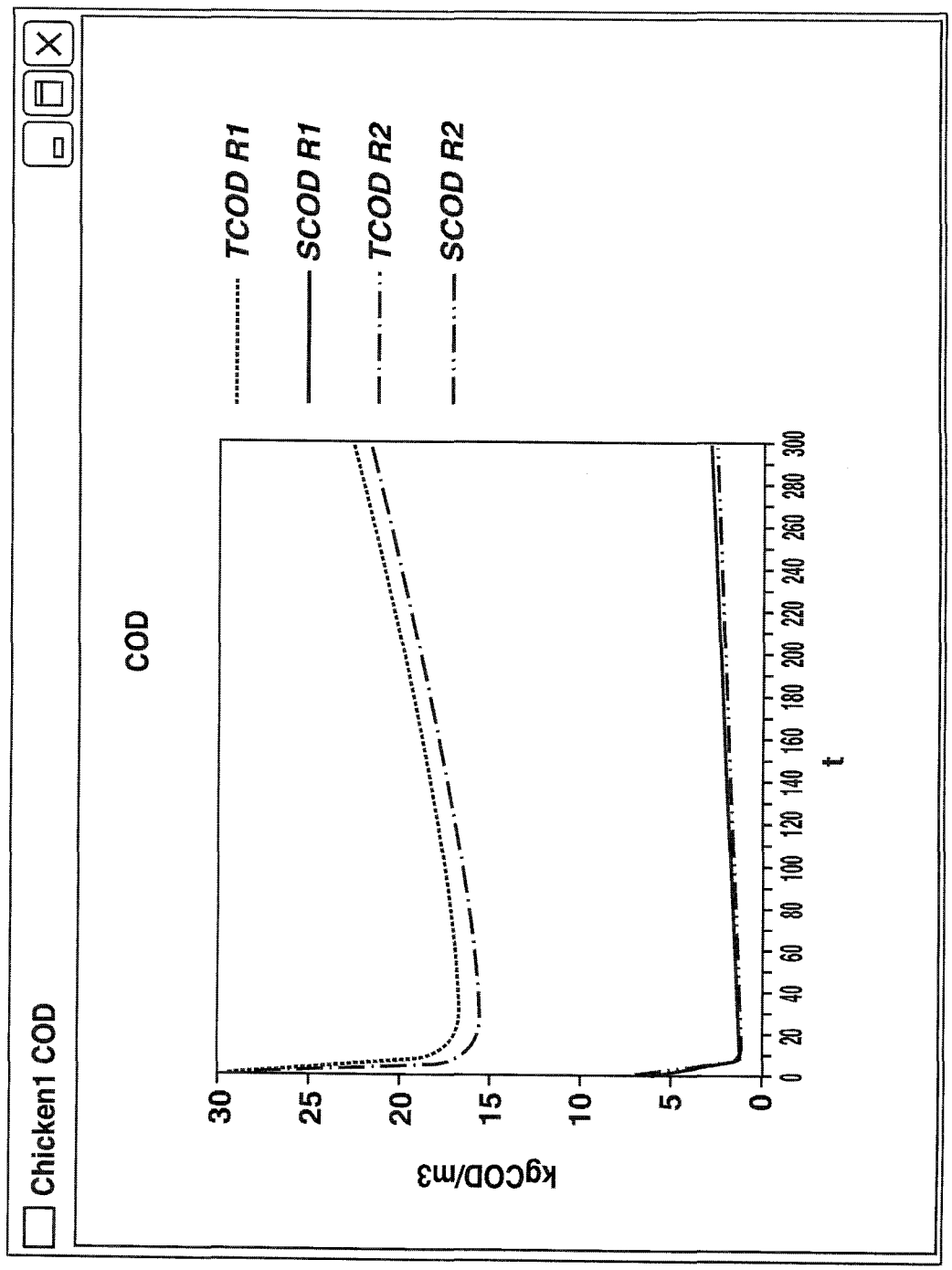
FIG. 6 is a graph illustrating modelling data of COD in Reactor 1 and Reactor 2.

The Chemical Oxygen Demand (COD) indicates organic pollutants. The COD values obtained from Reactor 1 and Reactor 2 are shown in FIG. 6. The highest and second highest lines represent the Total Chemical Oxygen Demand (TCOD) for Reactors 1 and 2, respectively, whereas the second lowest and lowest lines represent the Soluble Chemical Oxygen Demand (SCOD) for Reactors 1 and 2, respectively.

The Soluble Chemical Oxygen Deman (SCOD) of 2 kgCOD/$m^3$ is low. In the future, decreasing COD levels could be beneficial but it is not of concern when liquid is land applied as a fertilizer. Total COD concentration of a traditional wet-fertilizer is between 20 and 30 kgCOD/$m^3$.

Organic Acids

Figure 7:
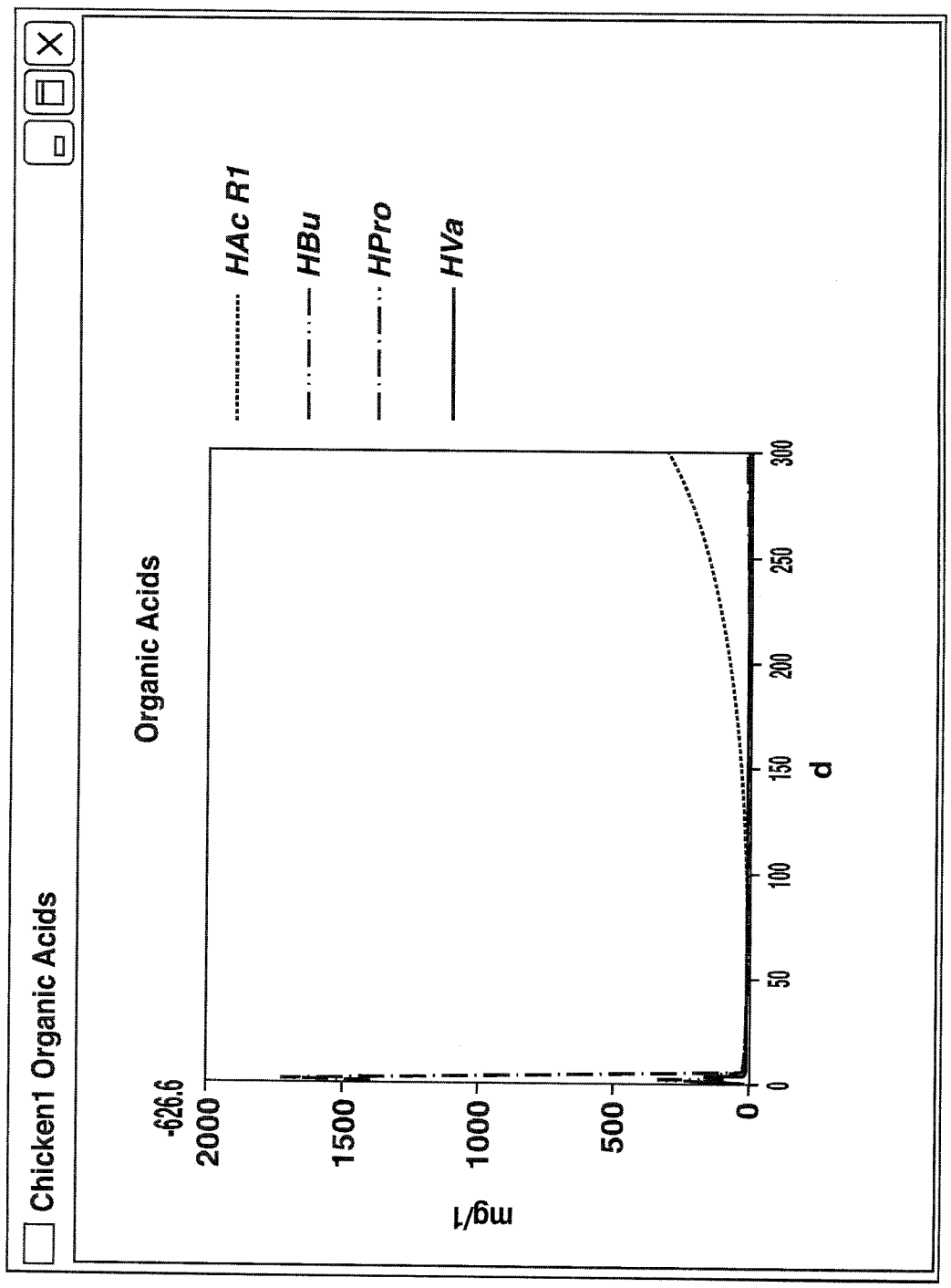
FIG. 7 is a graph illustrating modelling data of organic acid concentration in Reactor 1.

The buildup of acids is shown graphically in FIG. 7. There is a small build-up of acetate, however all other acids are at very low concentration further indicating system stability. The acetate levels shown in the model do not reach inhibition within 300 days. In FIG. 7, HAc represent acetate concentration, HBu represents butyrate concentration, HPro represent propionate concentration, and HVa represents valerate concentration.

Inhibitions

Figure 8:
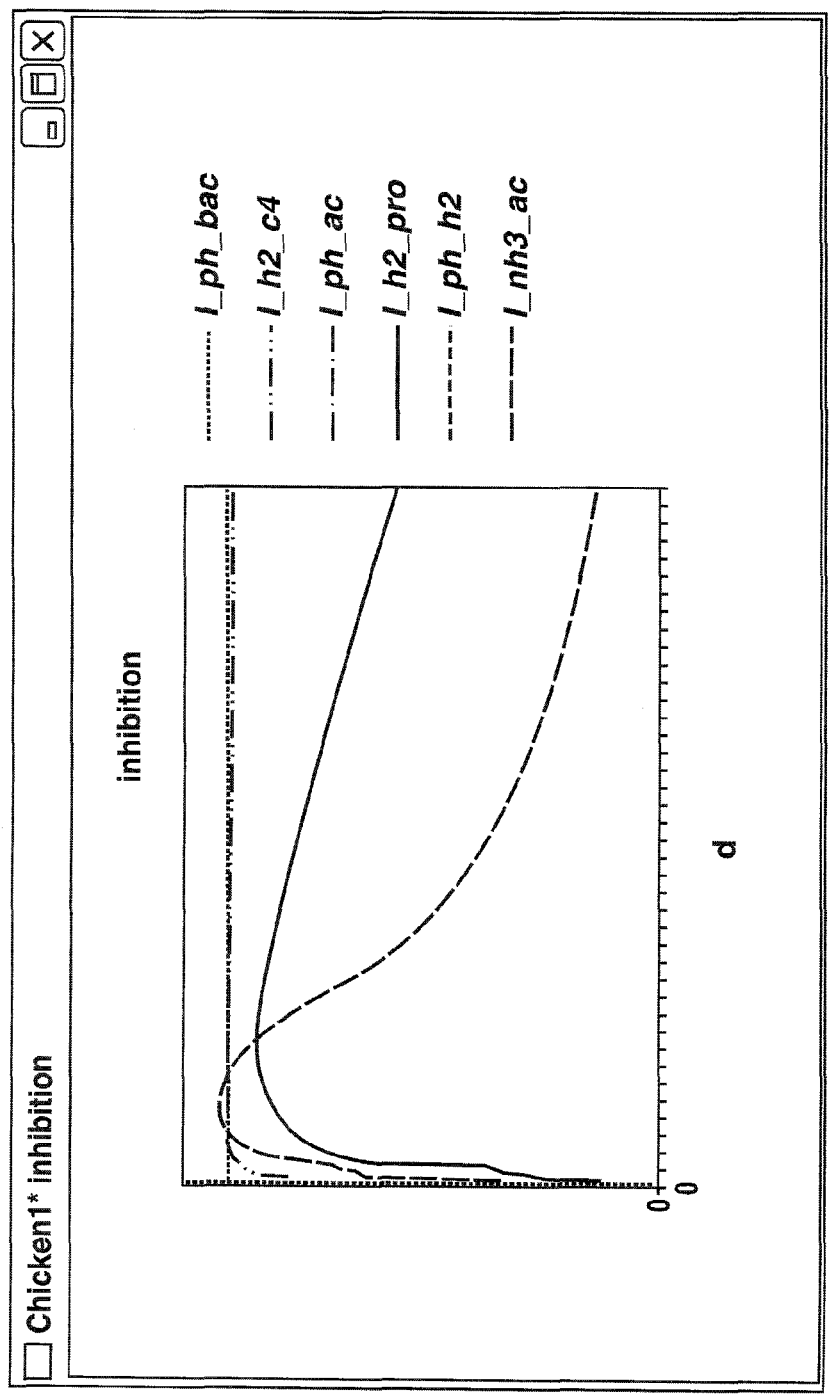
FIG. 8 is a graph illustrating modelling data of inhibition levels of certain compounds during anaerobic digestion.

FIG. 8 shows how various components of the digestion process affect one another. This graph shows the activity of a reaction, therefore the line representing 1_nh3_ac below is largely inhibited while the 1_ph_h2 and 1-h2_c4 lines indicate that these reactions are not inhibited. The major inhibition is due to $NH_3$ inhibiting the chemical-biological process of acetoclastic methanogenesis (the breakdown of acetate into methane and carbon dioxide). The inhibition shown corresponds with the buildup of acetate shown in FIG. 7. It is normal in anaerobic digestion to have certain levels of inhibition. The inhibition shown in FIG. 8 does not result in system instability as no significant accumulation of acids is observed in FIG. 7. In FIG. 8 1_ph_bac represents pH inhibition of acetogens and acidogens, 1_ph_h2 represents pH inhibition of degrading organisms, 1_ph_ac represents inhibition of acetate degrading organisms, 1_h2_c4 represents hydrogen inhibition for C4+ degradation, 1_h2_pro represents hydrogen inhibition of propionate OHPA, and 1_nh3_ca represents NH3 inhibition of acetoclastic methanogenesis.

Acidity (pH)

Figure 9:
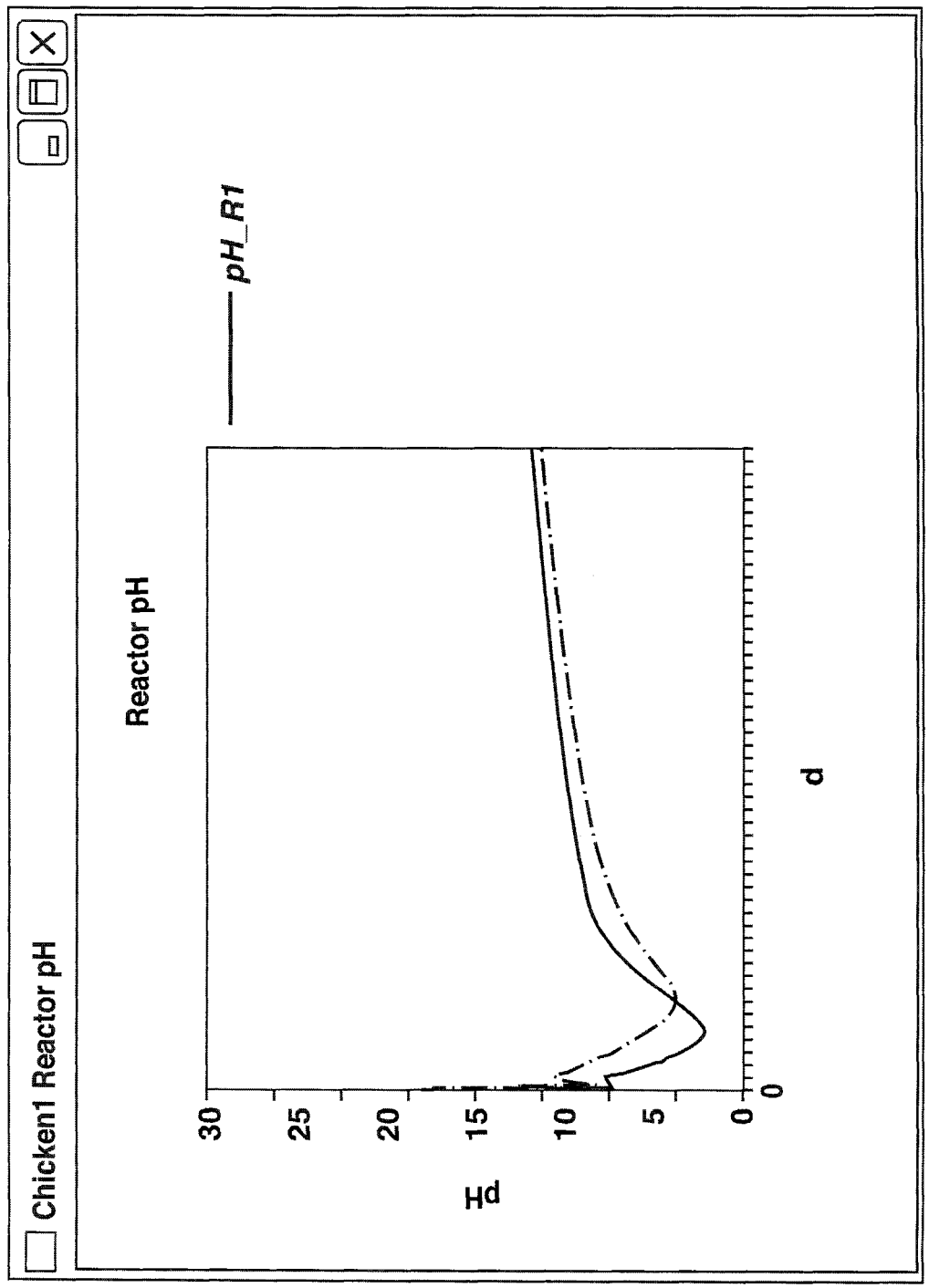
FIG. 9 is a graph illustrating modelling data of Reactor 1 pH level.

FIG. 9 shows the pH level in Reactor 1. The pH is a strong indicator of system stability and shows that system stability is achieved at around 50 days at approximately a pH of 7.5.

MAP Precipitation

Figure 10:
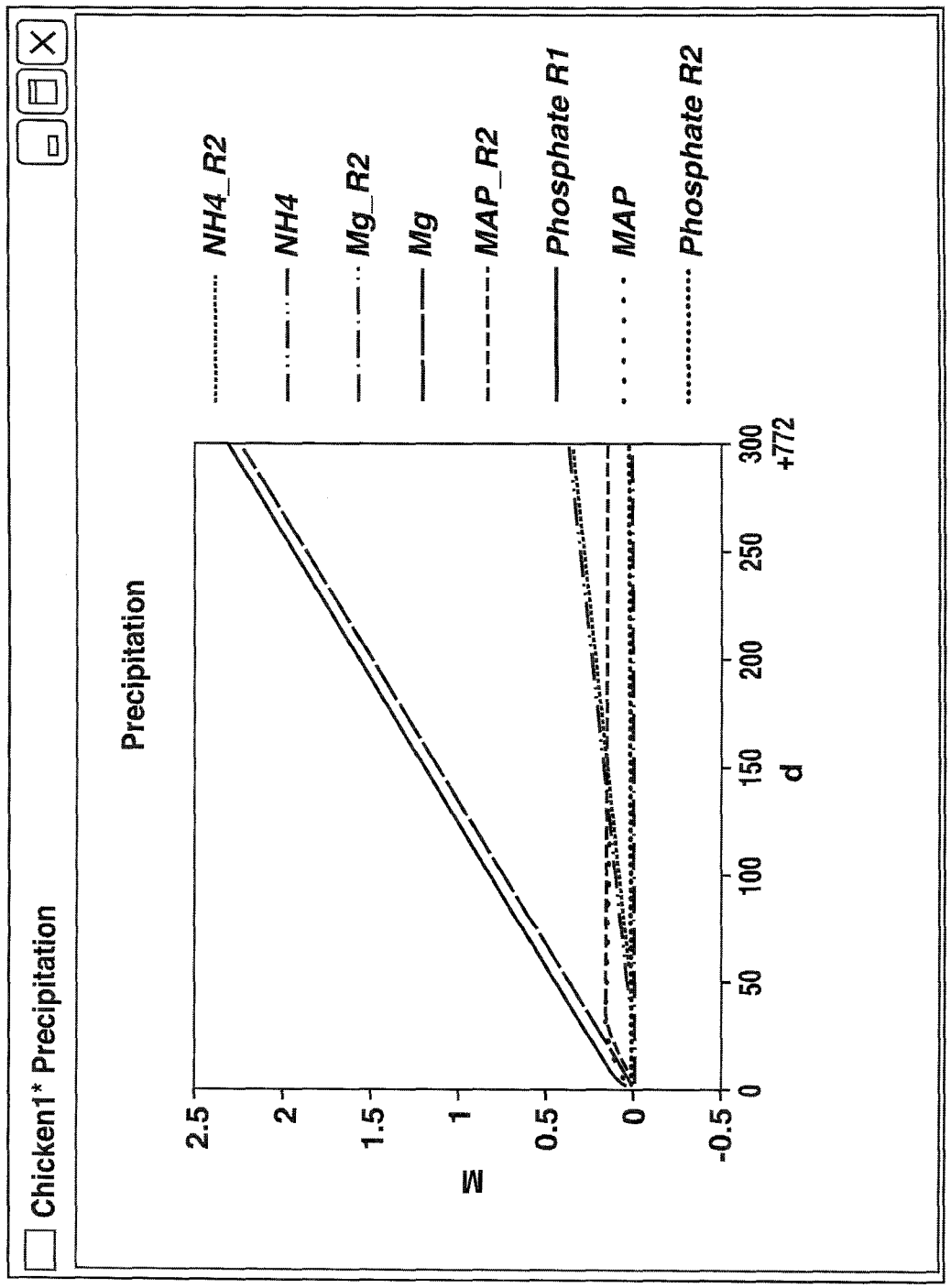
FIG. 10 is a graph illustrating modelling data of precipitation in Reactor 1 and Reactor 2.

FIG. 10 shows the precipitation of MAP in both, Reactor 1 and Reactor 2. The addition of MAP precipitation in the anaerobic digestion of chicken manure results in decreased ammonia concentrations, increased biogas production and an increase in overall system stability.

Figure 11:
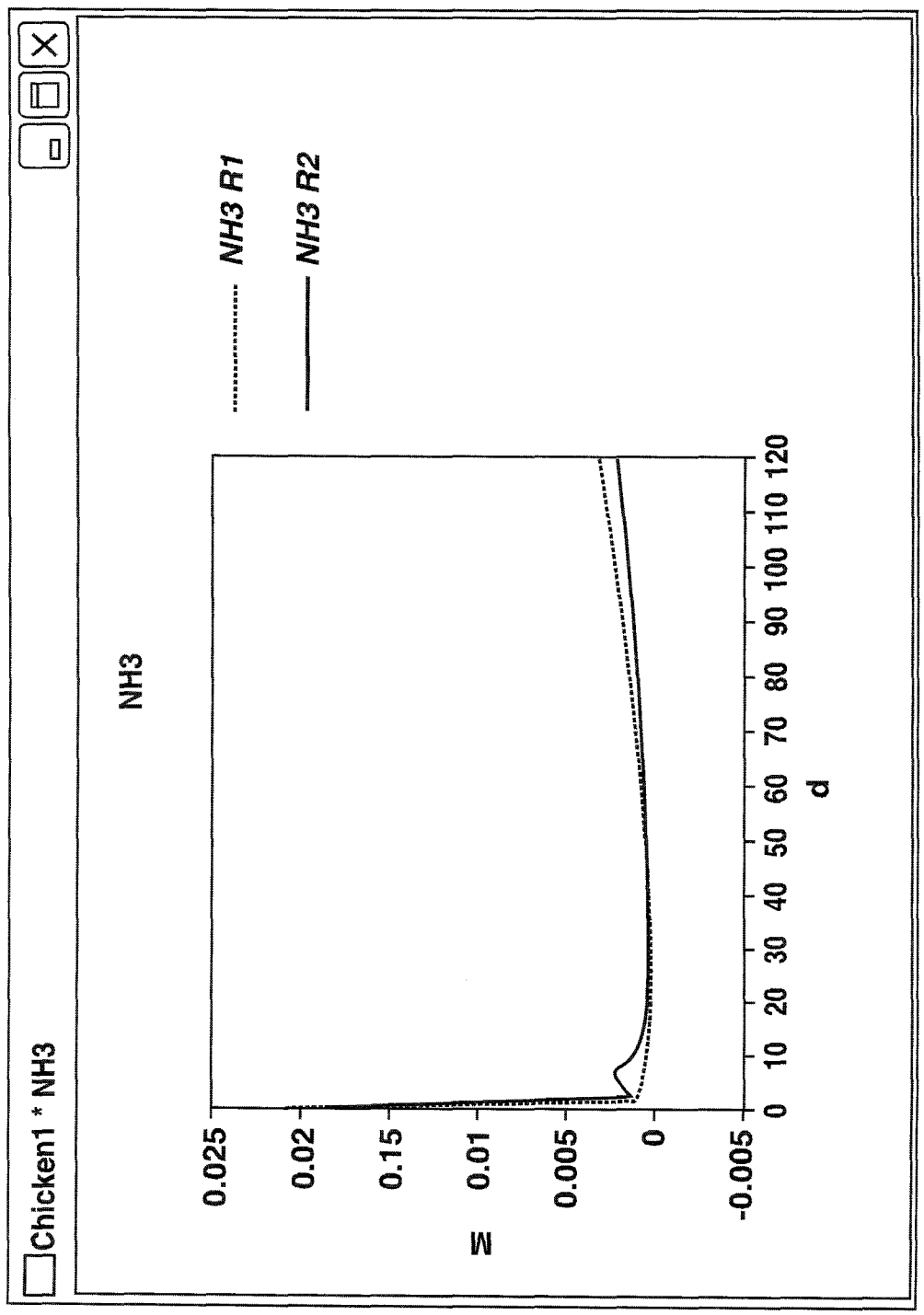
FIG. 11 is a graph illustrating modelling data of $NH_3$ concentration in Reactor 1 and Reactor 2.

FIG. 11 shows that there is very little build-up of ammonia within the system. Mg remains as the limiting compound for the formation of MAP while Phosphate and $NH_3$ show moderate levels of build up.

Conclusions

Feasibility of using chicken manure as a substrate in an anaerobic biodigester was studied. High concentrations of nitrogen in the chicken manure produced unstable conditions when modeling traditional anaerobic digestion in Aquasim, the simulation software used in this study. As such, conventional one reactor systems were deemed ineffective in treating chicken manure. Low gas yields result in questionable economics for this type of system, however, the incorporation of additional reactors and the utilization of MAP precipitation resulted in the stable and efficient system operation.

Simulated results in Aquasim of a 10 $m^3$/day input of chicken manure at 37° C. in a multiple-stage reactor system with individual volumes of 3000 $m^3$, 2000 $m^3$ and 2000 $m^3$, respectively, produced 470 $m^3$ of biogas per day. This system, with a 94% internal recycling rate, produced consistent gas flow over 300 days with minimal buildup of acids. Additional magnesium input (33 kgCOD/$m^3$) was used to stabilize the system and increase gas yields by way of MAP precipitation.

Gas yields were consistent with theoretical published predictions considering the difficulty in using chicken manure as an anaerobic digester feedstock. In previous in-house calibration studies, Aquasim was found to be approximately 90% accurate. As a dynamic model simulation, this system produced high gas yields and solved most, if not all, the problems associated with chicken manure.

The simulated results of the chicken manure in the multiple reactor system configuration produced reliable data and forecast stable biogas production. Through the use of MAP precipitation, ammonia levels have been decreased to acceptable levels. Although there are still inhibitions due to ammonia levels, further mitigation becomes increasingly difficult.

Utilizing MAP precipitation to remove ammonia works well in a dynamic simulated model and it is recommended to be implemented in a real reactor. However, magnesium, at $370/tonne, limits the viability of any large scale operations because struvite (MAP) production yields $320/tonne. Other resources for magnesium input were explored such as seawater bittern waste. The in-house calibrated model of Aquasim which has proven to produce accurate results within 10%, suggests that this system is technically feasible.

EXPERIMENTAL DATA

Several laboratory tests were carried out to observe the operation and utility of anaerobic digestion solutions.

The first test consisted of two bottle tests, run simultaneously. The purpose of the test was to confirm that biogas is produced from the solids as opposed to the liquids. The substrate was separated into solids and liquids by passing it through a semi-permeable membrane, referred to as the "inner bag". Isolated liquid and solids were then put into separate bottles. Each of the bottles acted as the "outer bag" of the digestion system, which collects produced biogas. The first bottle contained only solid material (digested sludge, manure and polymers) that remained in the "inner bag". The second bottle contained only liquid leachate that passed through the wall of the "inner bag". Neither bottle contained the actual "inner bag" itself.

It was found that the solid waste material in the first bottle produced a significantly greater amount of biogas as compared to the liquid leachate in the second bottle. These results indicate that the digestible biomass is being retained in the "inner bag" and that biogas can be produced in the absence of larger amounts of liquids. Results of the test are demonstrated in Table 2.

TABLE 2

Biogas Production Comparison - Solid & Liquid Material - Bottle Tests

| Day | Solid Material ($cm^3$) | Liquid Leachate ($cm^3$) |
| --- | --- | --- |
| Day 1 | 0 | 0 |
| Day 2 | 330.2 | 61.0 |
| Day 3 | 625.6 | 102.5 |
| Day 4 | 960.1 | 144.1 |

A second test was carried out to demonstrate that the presence of the "inner bag" does not inhibit biogas production. The setup of the second test was similar to the first test outlined above in that it involved two bottle tests. Each of the bottles acted as the "outer bag" of the digester system, which collects produced biogas. One bottle contained the "inner bag" made of geotextile membrane and the solid waste it retained (digested sludge, manure and polymers). The second bottle contained only the solid waste material without the "inner bag". Biogas yields were similar for both bottle tests, demonstrating that the presence of the "inner bag" does not inhibit biogas production. Although the data in Table 3 shows higher yields for the waste material without the "inner bag", this difference is minimal and is likely due to the inhomogeneous nature of the samples and inherent inaccuracy with measuring techniques.

TABLE 3

Biogas Production Comparison - Inclusion of Inner Bag - Bottle Tests

| Day | Solid Material w/ "Inner Bag" ($cm^3$) | Solid Material w/o "Inner Bag" ($cm^3$) |
| --- | --- | --- |
| Day 1 | 149.2 | 159.6 |
| Day 2 | 217.0 | 238.6 |
| Day 3 | 272.5 | 307.4 |
| Day 4 | 321.2 | 364.7 |
| Day 5 | 350.6 | 406.1 |
| Day 6 | 384.9 | 454.1 |
| Day 7 | 421.0 | 501.5 |
| Day 8 | 433.3 | 525.9 |
| Day 9 | 448.2 | 551.1 |
| Day 10 | 458.8 | 572.7 |
| Day 11 | 487.2 | 607.6 |
| Day 12 | 496.2 | 622.9 |
| Day 13 | 514.7 | 643.3 |
| Day 14 | 517.4 | 649.0 |

The third test was performed to evaluate the biogas production in a double-bag system, as outlined above with reference to the figures. The "outer bag" was composed of the EDPM membrane material that is used in traditional anaerobic digester roof construction and the "inner bag" was composed of geotextile membrane. The "inner bag" contained the solids from the waste material (digested sludge, manure and polymers). The liquid leachate was drained into a separate container before the "inner bag" was placed in the "outer bag" and sealed. The test showed that after one day, the "outer bag" was full of biogas. No quantitative results were recorded, simply a visual examination that showed the "outer bag" had expanded in one day.

The fourth test was very in nature to the third, but was carried out using a different type of manure. Biogas was produced within the first day. Visual examination showed that the "outer bag" had expanded in one day.

The present invention has been described with regard to a plurality of illustrative embodiments. However, it will be apparent to persons skilled in the art that a number of variations and modifications can be made without departing from the scope of the invention as defined in the claims.

I claim:

1. An anaerobic treatment system for treating organic substrate, the system comprising:
   i) a receiving tank for receiving the substrate to be treated and generating a slurry together with a liquid;
   ii) a first digester tube in liquid communication with the receiving tank for receiving the slurry for storage/hydrolysis, the first digester tube comprising:
      an inner bag permeable to gas and liquid and substantially impermeable to solids, wherein the inner bag does not include a mixer or agitator; and
      an outer bag housing the inner bag such that gas and liquid leaches from the inner bag to the outer bag, the outer bag impermeable to gas and liquid; and
   iii) a drainage system in communication with the outer bag, the draining system comprising a drain valve operable in a closed position for preventing draining of the outer bag and in an open position for draining the outer bag of leachate;
   wherein, when the drainage system is closed, the slurry in the first digester tube is separated into leachate collected in the outer bag and substrate collected in the inner bag.

2. The anaerobic treatment system of claim 1, further comprising:
   iv) a second digester tube in fluid communication with the receiving tank, the second digester tube comprising:
      an inner bag permeable to gas and liquid and substantially impermeable to solids; and
      an outer bag housing the inner bag such that gas and liquid leaches from the inner bag to the outer bag, the outer bag impermeable to gas and liquid; and
   v) a drainage collection tank in fluid communication with the drainage system for receiving leachate drained from the digester tubes, the drainage collection tank in fluid communication with the receiving tank for recycling leachate to the receiving tank, and in fluid communication with the digester tubes for recycling leachate to the digester tubes;
   wherein the second digester tube is suitable for methanization treatment of the slurry.

3. The anaerobic treatment system of claim 2, further comprising:
   vi) a third digester tube in fluid communication with the receiving tank, the third digester tube comprising:
      an inner bag permeable to gas and liquid and substantially impermeable to solids; and
      an outer bag housing the inner bag such that gas and liquid leaches from the inner bag to the outer bag, the outer bag impermeable to gas and liquid; and
   wherein the drainage collection tank is in fluid communication with the inner bag of the third digester tube for recycling leachate from the third digester tube for digestate treatment with biologically activated sludge and a microorganism for digesting the leachate.

4. The anaerobic treatment system of any one of claim 1, 2 or 3 wherein the digester tubes are sloped towards one end for collecting the leachate and the draining system collects the leachate from the lower end.

5. The anaerobic treatment system of any one of claim 1, 2, or 3, wherein the inner bag is substantially impermeable to solids having a particle size greater than 0.425 mm.

6. The anaerobic treatment system of claim 1, wherein the inner bag is substantially impermeable to solids having a particle size greater than 0.425 mm.

* * * * *